US 10,743,946 B2

(12) United States Patent
Harrah et al.

(10) Patent No.: US 10,743,946 B2
(45) Date of Patent: Aug. 18, 2020

(54) MEDICAL USER INTERFACES AND RELATED METHODS OF USE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Sandesh Gavade, Bangalore (IN); Pavan Misra, Bangalore (IN); Abhijit Takale, Pune (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/290,430

(22) Filed: Mar. 1, 2019

(65) Prior Publication Data
US 2019/0192237 A1    Jun. 27, 2019

Related U.S. Application Data

(63) Continuation of application No. 15/416,838, filed on Jan. 26, 2017, now Pat. No. 10,258,415.
(Continued)

(51) Int. Cl.
*A61B 34/00* (2016.01)
*G06T 11/60* (2006.01)
(Continued)

(52) U.S. Cl.
CPC .............. *A61B 34/25* (2016.02); *A61B 18/26* (2013.01); *G06T 7/0014* (2013.01); *G06T 7/60* (2013.01); *G06T 11/60* (2013.01); *G16H 40/63* (2018.01); *A61B 6/464* (2013.01); *A61B 6/465* (2013.01); *A61B 17/22004* (2013.01); *A61B 2018/00505* (2013.01); *A61B 2018/00511* (2013.01); *A61B 2018/00517* (2013.01); *A61B 2018/00577* (2013.01); *A61B 2018/00982* (2013.01); *A61B 2034/107* (2016.02); *A61B 2034/2065* (2016.02); *A61B 2034/2074* (2016.02);
(Continued)

(58) Field of Classification Search
None
See application file for complete search history.

(56) References Cited

U.S. PATENT DOCUMENTS

2003/0149352 A1   8/2003   Liang et al.
2007/0270897 A1   11/2007  Skerven et al.
(Continued)

FOREIGN PATENT DOCUMENTS

WO   WO 2013/154708 A1   10/2013

*Primary Examiner* — Yingchun He
(74) *Attorney, Agent, or Firm* — Bookoff McAndrews, PLLC

(57) ABSTRACT

A medical system for use in a lithotripsy procedure may include a processor configured to receive input from a first imaging device, wherein the first imaging device may be configured to send image data representative of an image captured in a lumen of a kidney, bladder, or ureter to the processor. The processor may be configured to display the image on a display device coupled to the processor, and analyze the image to sense the presence of an object within the image. If an object was sensed within the image, the processor may analyze the image to estimate a size of the object, and display the estimate on the display device.

17 Claims, 11 Drawing Sheets

Related U.S. Application Data

(60) Provisional application No. 62/288,654, filed on Jan. 29, 2016.

(51) Int. Cl.

| | | |
|---|---|---|
| *G06T 7/60* | (2017.01) | |
| *G16H 40/63* | (2018.01) | |
| *A61B 18/26* | (2006.01) | |
| *A61B 6/00* | (2006.01) | |
| *A61B 34/20* | (2016.01) | |
| *A61B 34/10* | (2016.01) | |
| *A61B 18/00* | (2006.01) | |
| *A61B 17/22* | (2006.01) | |
| *G06T 7/00* | (2017.01) | |

(52) U.S. Cl.
CPC ... *A61B 2034/252* (2016.02); *A61B 2034/254* (2016.02); *A61B 2034/256* (2016.02); *A61B 2217/007* (2013.01); *A61B 2218/002* (2013.01); *G06T 2207/10116* (2013.01); *G06T 2207/30084* (2013.01); *G06T 2210/41* (2013.01)

(56) References Cited

U.S. PATENT DOCUMENTS

| | | |
|---|---|---|
| 2008/0226029 A1 | 9/2008 | Weir et al. |
| 2011/0295302 A1 | 12/2011 | Mohl |
| 2013/0315440 A1 | 11/2013 | Frank et al. |
| 2014/0276101 A1 | 9/2014 | Asselin et al. |
| 2015/0196250 A1 | 7/2015 | Nair |
| 2015/0313444 A1 | 11/2015 | Wolf |

MEDICAL USER INTERFACES AND RELATED METHODS OF USE

CROSS-REFERENCE TO RELATED APPLICATION(S)

This patent application is a continuation of U.S. application Ser. No. 15/416,838, filed Jan. 26, 2017 which claims the benefit under 35 U.S.C. § 119 to U.S. Provisional Patent Application No. 62/288,654, filed on Jan. 29, 2016, all of which are incorporated by reference herein in their entireties.

TECHNICAL FIELD

Examples of the present disclosure relate generally to medical user interfaces and related methods of use. More particularly, examples of the present disclosure relate to medical user interfaces for use in lithotripsy procedures.

BACKGROUND

Many patients develop stones within their common bile, urinary, renal or ureteral systems. These stones may block ducts and cause great pain and therefore must be removed. Several approaches are available for treating such stones, including, laser treatment and subsequent removal of the stones from the body. These lithotripsy procedures are often performed with the aid of an endoscopic device, and an endoscopic operating field may be displayed to an operator. Sizing objects in the endoscopic operating field may be important to the treatment. However, current methods of sizing objects in the operating field are inaccurate and/or cumbersome.

Thus, there remains a need for improved methods and devices for sizing objects during lithotripsy procedures.

SUMMARY OF THE DISCLOSURE

In one aspect, the present disclosure is directed to a medical system for use in a lithotripsy procedure. The medical system may include a processor configured to receive input from a first imaging device, wherein the first imaging device may be configured to send image data representative of an image captured in a lumen of a kidney, bladder, or ureter to the processor. The processor may be configured to display the image on a display device coupled to the processor, and analyze the image to sense the presence of an object within the image. If an object was sensed within the image, the processor may analyze the image to estimate a size of the object, and display the estimate on the display device.

The processor may be configured to receive a virtual boundary of the object on the displayed image from a user, and wherein the processor may be configured to estimate the size of the object based on the virtual boundary. The processor may be configured to compare the image to a database of images to determine the presence of the object within the image. The object may be a ureteral orifice. The object may be a stone. The processor may be configured to update the estimate of the size of the stone in real-time while fragments of the stone are being removed by the application of a laser to the stone. The processor may be configured to update the estimate of the size of the stone based upon a proportion of the image that is occupied by the stone. The processor may be configured to analyze the image to sense when fragments of the stone have been removed by the laser. The processor may be configured to analyze the image to estimate a size of the removed fragments. The processor may be configured to generate a scaled grid that is configured to be overlaidoverlaid onto the image displayed on the display device. The scaled grid may be representative of an actual size of objects within the image. The processor may be configured to regenerate the scaled grid whenever the processor senses that the first imaging device has been moved. The processor may be configured to receive x-ray data representative of an x-ray image from an x-ray imaging device, and may be configured to simultaneously display the image alongside the x-ray image on the display device. The object may be an orifice, and wherein the processor may be further configured to analyze the image containing the orifice and generate recommended parameters for inflating a balloon that is inserted into the orifice. The recommended parameters may include a length of time for inflating the balloon.

In another aspect, the present disclosure is directed to a medical system for use in a lithotripsy procedure performed on a patient. The medical system may include a processor configured to receive input from a first imaging device, wherein the first imaging device may be configured to send image data representative of an image captured in a lumen of a kidney, bladder, or ureter to the processor. The processor may be configured to display, on a display device coupled to the processor, an ablation user interface during an ablation portion of the lithotripsy procedure, the ablation portion of the lithotripsy procedure including inserting a balloon into the patient, wherein the processor may be configured to simultaneously display an image of the balloon disposed within the patient and a recommendation for a length of time to inflate the balloon on the ablation user interface.

The medical system may further include a second imaging device that is an x-ray imaging device configured to send x-ray data representative of an x-ray image to the processor. The processor may be further configured to display, on the display device, a first user interface before initiation of the lithotripsy procedure displaying information regarding the patient, and display, on the display device, a second user interface during a first portion of the lithotripsy procedure, wherein the second user interface may include one or more of the image and the x-ray image. The processor may be further configured to display, on the display device, a third user interface during a second portion of the lithotripsy procedure, the second portion of the lithotripsy procedure including inserting a guidewire into the lumen, and wherein the third user interface may include both an image and an x-ray image of the guidewire displayed simultaneously on the display device. The processor may be further configured to display, on the display device, a fifth user interface during a fourth portion of the lithotripsy procedure, wherein the fourth portion of the lithotripsy procedure may include ablating a stone with laser energy, wherein the fifth user interface may include an image of an energy delivery element delivering laser energy to the stone within the lumen. The processor may be configured to display, on the display device, a sixth user interface during a fifth portion of the lithotripsy procedure, wherein the fifth portion of the lithotripsy procedure may include delivering a stent into a lumen of the patient, wherein the sixth user interface may include an image of the stent while disposed within the patient. The processor may be further configured to display, on the display device, a seventh user interface after the lithotripsy procedure has concluded, wherein the seventh user interface may include data relating to the one or more of the first, second, third, ablation, or fifth portions of the lithotripsy procedure.

In yet another aspect, the present disclosure is directed to a method for displaying images relating to a lithotripsy procedure. The method may include analyzing an image received from an imaging device disposed within a lumen of a patient to sense the presence of an object within the image. If the object is sensed within the image, the method may further include analyzing the image to estimate a size of the object, and displaying the estimate on the display device.

The object may be a stone, and the method may further include updating the estimate of the size of the stone in real-time while fragments of the stone are being removed by the application of a laser to the stone. The method may further include analyzing the image to sense when fragments of the stone have been removed by the laser.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

The accompanying drawings, which are incorporated in and constitute a part of this specification, illustrate several examples of the present disclosure and together with the description, serve to explain the principles of the invention.

DESCRIPTION OF THE EXAMPLES

Reference will now be made in detail to examples of the present disclosure, which are illustrated in the accompanying drawings. Wherever possible, the same reference numbers will be used throughout the drawings to refer to the same or like parts.

Figure 1:
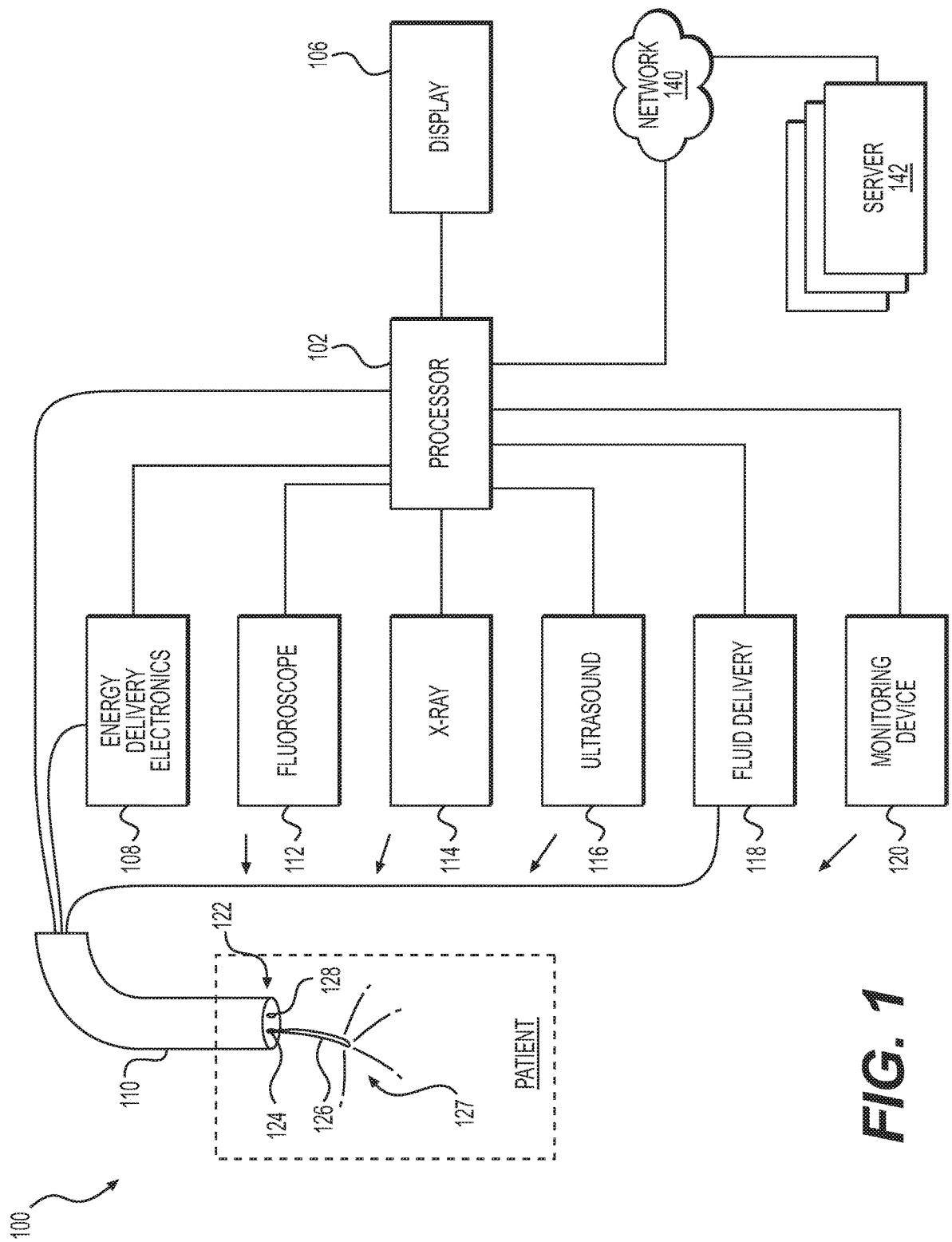
FIG. 1 is a schematic view of a system for performing a lithotripsy procedure according to one example of the present disclosure.

Examples of the present disclosure relate to devices and methods for controlling the application of energy to objects disposed within a body lumen of a patient, such as, e.g., a lumen of a kidney, a bladder, or a ureter. FIG. 1 illustrates a system 100 for delivering energy, in accordance with a first example of the present disclosure. The system may include a processor 102 that is operatively coupled to a display 106. In some examples, processor 102 and display 106 may be disposed within a single handheld unit, such as, e.g., a tablet computer such as a Microsoft Surface, iPAD® or iPHONE®. In other examples, processor 102 and display 106 may be modular and may connect to one another by any suitable mechanism. Display 106 may be a touchscreen input device that allows a user to send commands to processor 102. In other examples, a mouse and/or keyboard (not shown) may be operatively coupled to processor 102. Multiple display devices (with or without input capability) may be deployed at alternate sites in or out of the operating suite. This may include video output streams for broadcast to alternate pre-exiting/third party displays/locations.

Processor 102 also may be coupled to energy delivery electronics 108, an endoscopic device 110, a fluoroscope 112, an x-ray imaging device 114, an ultrasound device 116, a fluid delivery device 118, and a patient monitoring device 120.

Processor 102 may be generally configured to accept information from the system and system components, and process the information according to various algorithms to produce control signals for controlling energy delivery electronics 108, endoscopic device 110, fluoroscope 112, x-ray imaging device 114, ultrasound device 116, fluid delivery device 118, and patient monitoring device 120. The processor 102 may accept information from the system and system components, process the information according to various algorithms, and produce information signals that may be directed to visual indicators, digital displays, audio tone generators, or other indicators of, e.g., a user interface, in order to inform a user of the system status, component status, procedure status or any other useful information that is being monitored by the system. The processor 102 may be a digital IC processor, analog processor or any other suitable logic or control system that carries out the control algorithms.

Energy delivery electronics 108 may include an optical energy source, such as, e.g., a holmium (Ho) laser source, a holmium:YAG (Ho:YAG) laser source, a neodymium-doped:YAG (Nd:YAG) laser source, a semiconductor laser diode, a potassium-titanyl phosphate crystal (KTP) laser source, a carbon dioxide (CO2) laser source, an Argon laser source, an Excimer laser source, a diode laser source, or another suitable laser source. In some examples, the laser source may be a laser diode. The laser diode may illuminate a target area, and may be mounted at the distal end of a catheter or other suitable elongate member, such as, e.g., endoscopic member 110. In some examples, a high power (e.g., superluminescent) LED may be used in place of a laser source. In some examples, an intense, pulsed light source may be used in place of a laser source.

In an alternative example, energy delivery electronics 108 may be a pneumatic control device for performing lithotripsy procedures by direct contact of a probe with a targeted stone. In this alternative example, processor 102 may control air pressure and frequency as well as irrigation activation and flowrate. The processor 102 may also be able to connect via the network 140 to the hospital server 142 and obtain patient related data from the HIS, PACS and EMR. This data can then be processed and displayed on the display device 106. The system may also allow the processor 102 to send updated data based on the procedure statistics and information back to the HIS, PACS and EMR.

Energy delivery electronics 108 may be configured to control delivery of any other suitable energy modality, such as, e.g., ultrasound.

Endoscopic device 110 may be any suitable endoscopic member, such as, e.g., an endoscope, a ureteroscope, a nephroscope, a colonoscope, a hysteroscope, a uteroscope, a bronchoscope, a cystoscope, a sheath, or a catheter. Endoscopic device 110 may include one or more additional lumens configured for the passage of a variety of surgical equipment, including, but not limited to, imaging devices and tools for irrigation, vacuum suctioning, biopsies, and drug delivery. At least a portion of endoscopic device 110 may be radiopaque.

An energy delivery fiber 126 (e.g., a laser fiber) may extend from distal end 122 of endoscopic device 110 through a lumen 124, and may be configured to deliver laser energy 127 at a distal end. Energy delivery fiber 126 may include a light source channel that is configured to receive light or laser energy at a proximal end, and transmit the light or laser energy to a distal end via internal reflection within the fiber. Energy delivery fiber 126 may receive energy transmitted from energy delivery electronics 108, and may deliver the received energy to a desired treatment location, such as, e.g., a stone.

An imaging device 128 may also be disposed at the distal end 122 of endoscopic device 110. The imaging device may include any suitable device configured to provide images to processor 102 for display on display 106 including, e.g., a CMOS imaging sensor or other solid state device and one or more glass or polymeric lenses that produce electronic image signals representative of an image of the tissue or other objects in front of the imaging device 128. The imaging device 128 may be a low light sensitive, low noise video VGA, CMOS, color imager or higher resolution sensor such as SVGA, SXGA, or XGA. The video output of the imaging device 128 may be in any conventional format including PAL, NTSC or high definition video format, and may be transmitted to processor 102 by any wired or wireless mechanism. X-ray imaging device 114 may detect the x-rays generated by fluoroscope 112 and may be able to create an x-ray image of the treatment areas and of endoscopic device 110. Image information detected by x-ray imaging device 114 may be provided to processor 102.

Fluid delivery system 118 may include an irrigation pump (not shown) that may be configured to provide irrigation fluid to a body lumen and/or to evacuate the fluid from the body lumen via lumens or channels of endoscopic device 110. More specifically, activation of the pump by a user may send saline or another suitable irrigation fluid through endoscopic device 110. Ultrasound device 116 may be any suitable device configured to produce a real-time ultrasound image of body tissues and lumens. Monitoring device 120 may include sensors configured to measure the blood pressure, pulse rate, temperature, and peripheral capillary oxygen saturation (Sp02), among other patient vitals. Portions of monitoring device 120 may be disposed on the skin of the patient, within the patient, or may be positioned off of the patient.

Processor 102 may be coupled to one or more servers 142 via a network 140, such as, the Internet. Servers 142 may provide various information to processor 102 such as, e.g., electronic medical records of the patient, among other information. The electronic medical records may include standard medical and clinical data gathered by one or more health care providers for the patient, and may constitute a comprehensive medical history for the patient. The electronic medical records may include patient information pertinent to the physician performing a lithotripsy procedure, such as, previous history of stones, allergies to anesthesia, whether the patient is on blood thinners, among other information.

FIGS. 2-11 depict various user interfaces that may be shown on display 106 over the course of a medical procedure, such as, e.g., during a lithotripsy procedure for breaking and removing stones from the kidney, bladder, or ureter. The user interfaces may allow a physician to perform the various stages of a lithotripsy procedure using a single display and control console.

Figure 2:
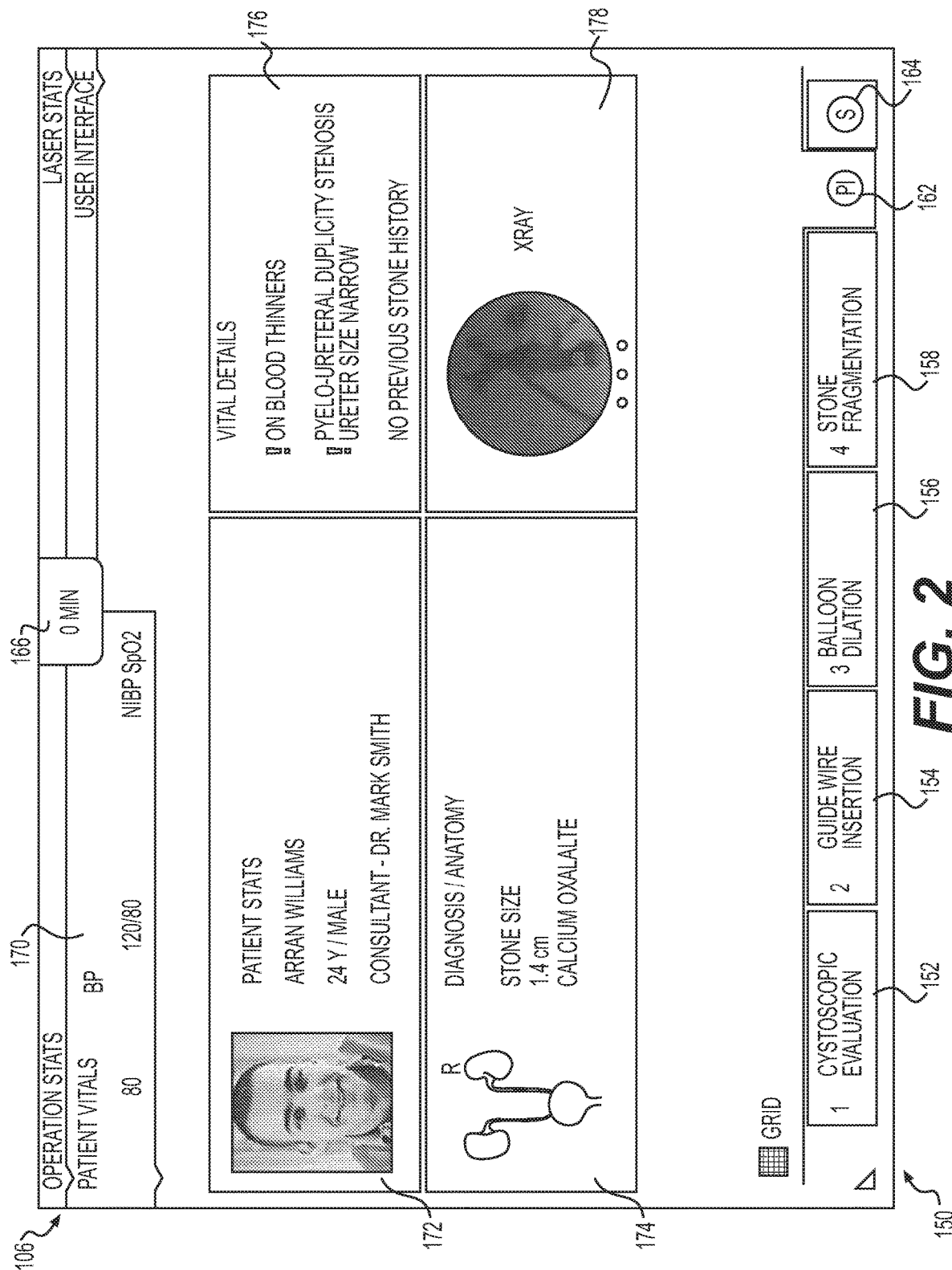
FIGS. 2-11 are exemplary user interfaces that may be used with the system of FIG. 1.

FIG. 2 depicts an exemplary user interface displayed on display 106 before a lithotripsy procedure is initiated. The user interface may include a procedure section 150 having multiple tabs that may be selected by a user, via e.g., a touchscreen of display 106. The tabs may correspond to various user interfaces usable by a physician or operator during different portions of the lithotripsy procedure. For example, tab 152 may correspond to a first portion of the lithotripsy procedure, such as a cystoscopic evaluation portion of the lithotripsy procedure. Additional tabs 154, 156, 158, and 160 (tab 160 shown only in FIGS. 8-11) may also be shown which correspond to other portions of the lithotripsy procedure. For example, tab 154 may correspond to a guide wire insertion portion of the lithotripsy procedure, while tab 156 may correspond to a balloon dilation portion of the lithotripsy procedure. Further, tab 158 may correspond to a stone fragmentation portion of the lithotripsy procedure, while tab 160 may correspond to a stenting portion of the lithotripsy procedure. The user interface may also include a patient information tab 162 and a summary tab 164. One or more of tabs 152-164 may be displayed concurrently to a user, and may be selected by the user at any time. The selection of a given tab by the user may cause different user interfaces to be displayed on display 106. It is also contemplated that additional portions of the procedure may be embodied in additional tabs selectable by a user.

Referring specifically to FIG. 2, patient information tab 162 is shown to be selected, and a corresponding patient information user interface is displayed on display 106. The patient information user interface may include a procedure timer 166 and a patient vitals field 170. The patient information user interface may also include a patient stats field 172, a diagnosis/anatomy field 174, a details field 176, and an x-ray field 178.

In some examples, procedure timer 166 may display an elapsed time of the lithotripsy procedure. Procedure timer 166 may be started manually by an operator, or may start automatically upon a trigger event, such as, for example, when a patient is administered anesthesia. Procedure timer 166 may be displayed on all user interfaces during all portions of the procedure. Patient vitals field 170 may display one or more patient vitals collected by, e.g., patient monitoring device 120, among other devices. For example, one or more of the patient's heart rate, blood pressure (e.g., noninvasive blood pressure (NIBP)), and/or peripheral capillary oxygen saturation (Sp02), among other patient vitals, may be displayed in patient vitals field 170.

Patient stats field 172 may display one or more statistics relating to the patient undergoing the lithotripsy procedure which may be retrieved by processor 102 from servers 142 via network 140. One or more of the patient's photo, name, age, gender, date of birth, primary physician, specialty physician, among other information, may be provided in patient stats field 172. Diagnosis/anatomy field 174 may include information relating to a previous diagnosis of the patient relating to the lithotripsy procedure. For example, a visual representation of the kidneys may be shown and the kidney diagnosed as having a stone, e.g., the right kidney, may be highlighted in diagnosis/anatomy field 174. Additionally, other information relating to the diagnosed stones, such as a pre-procedure estimate of the stone size may also be displayed in diagnosis/anatomy field 174. Details field 176 may include other information pertinent to the lithotripsy procedure. For example, medical data specific to the patient that is relevant during a surgical procedure may displayed, such as, e.g., whether the patient is on blood thinners, whether the patient is allergic to anesthesia, whether the patient's ureter is known to be narrow, and whether the patient has a prior history of kidney stones. An x-ray field 178 may also be shown on the patient information user interface. X-ray field 178 may allow an operator to select from one or more previously taken x-ray images of the patient so that an operator may view those images and familiarize herself with the patient's anatomy prior to the start of the lithotripsy procedure.

Figure 3:
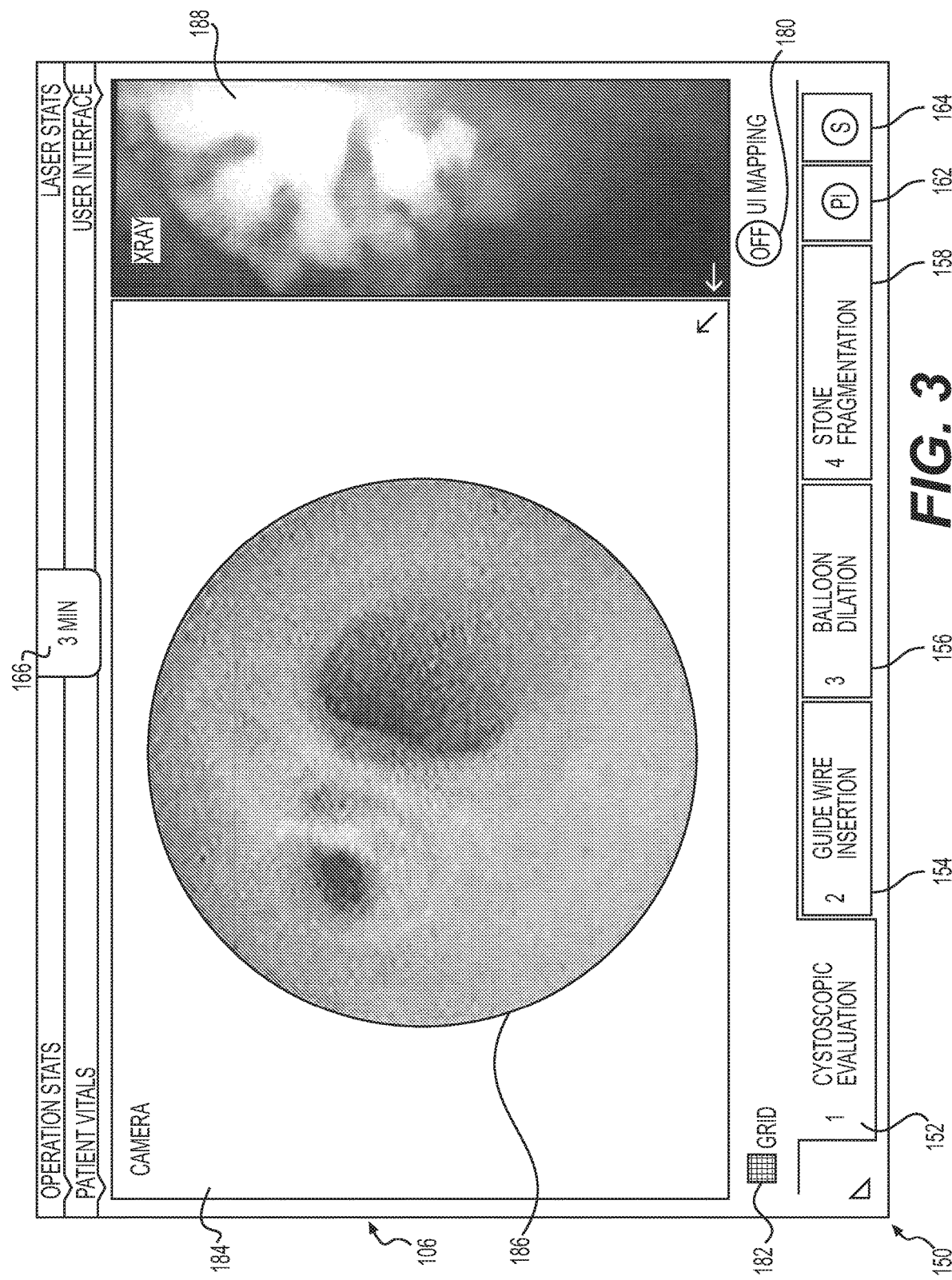

A user interface is shown in FIG. 3 which may correspond to an evaluation portion of the lithotripsy procedure. For example, the procedure may start with a visual evaluation of the kidney, bladder, or ureter, using an imaging device coupled to a cystoscope, ureteroscope, or the like. At this stage, the operator may select evaluation tab 152 to display one or more of a camera field 184 and an x-ray field 188 as shown in FIG. 3. In the example user interface shown in FIG. 3, the camera field 184 is shown as maximized, while only a portion of the x-ray field 188 is shown. This configuration may allow an operator to view a camera image 186 generated by, e.g., imaging device 128 shown in FIG. 1, on a larger proportion of display 106 for additional clarity. The user may select that x-ray field 188 be simultaneously displayed with camera field 184, or alternatively displayed instead of camera field 184, if desired. X-ray field 188 may be generated in real time by fluoroscope 112 and x-ray imaging device 114. The camera field 184 may allow a physician to visually perceive stone size and hardness, and may also allow the physician to determine the position of the energy delivery fiber 126 relative to the imaging device 128.

Once the lithotripsy procedure has begun, the user interface may further display a grid icon 182 and a mapping icon 180 that will be discussed in further detail below.

Figure 4:
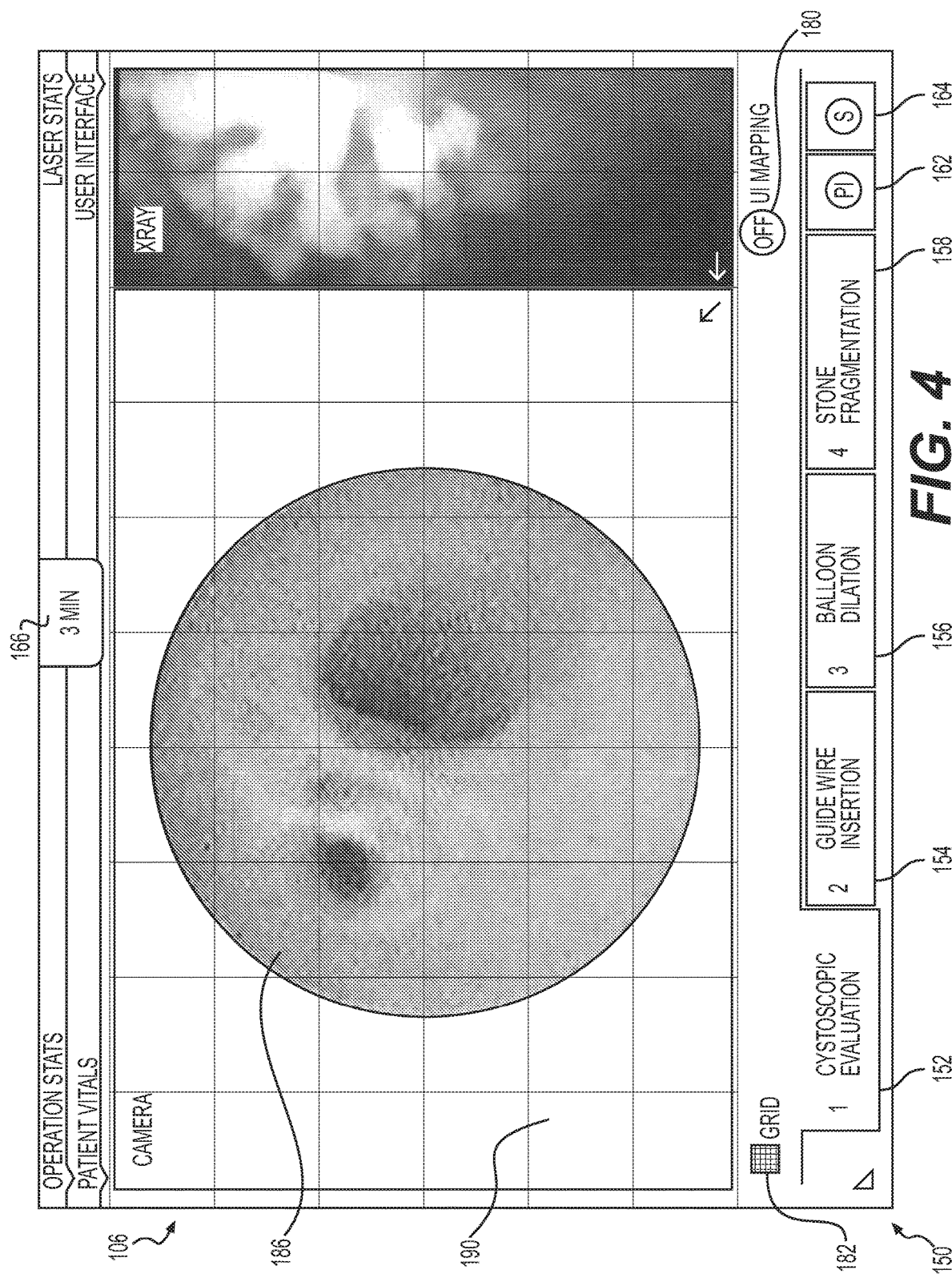

FIG. 4 depicts a user interface displayed on display 106 when an operator activates grid icon 182. In response to grid icon 182 being selected by a user during an evaluation portion of the lithotripsy procedure, a scaled grid 190 may be overlaidoverlaid onto at least a portion (or all) of camera image 186. The scaled grid may have one or more markings to allow an operator to quickly determine the actual size of an orifice, lumen, stone, or other object displayed on camera image 186. For example, the grid 190 may include a plurality of boxes, and the length of each box may correspond to an estimated distance within the lumen being displayed on camera image 186. For example, the length of one of the boxes on camera image 186 may correspond to, e.g., 1 mm within the lumen. The scaled grid 190 may be developed by processor 102 in real time using any suitable mechanism, including a reference object of known size in the viewing field, among other techniques. The scaled grid 190 may be updated in real time as the imaging device 128 is moved through the body in order to ensure accuracy. That is, each movement of imaging device 128 may require that the scaled grid 190 be reconfigured. For example, while disposed in a first position, the length of each box of scaled grid 190 may correspond to 1 mm within the lumen, but when the imaging device is moved to a second position (e.g., further distally in the lumen), the length of each box of scaled grid 190 may correspond to 1.2 mm within the lumen. In some examples, the length of each box on scaled grid 190 may be changed in order to represent the same distance within the image (e.g., 1 mm). In the example described above, the length of the boxes of scaled grid 190 would be larger when the imaging device is disposed in the first position than when the imaging device is disposed in the second position. In some examples, capture of an object of fixed reference may be needed to calculate and project the grid. To avoid depth based distortion, this may need to be calculated at a known distance or distances from the scope tip. Thus, the input of the devices visible in the surgical field (e.g., guidewire, basket, laser fiber) may be used. These devices may have markings on their shafts that would identify distance from scope tip that would be machine readable and independent of scope being used. These algorithms could be based on pre-programmed values for a given device(s) or through real-time acquisition from video stream. The scaled grid may be generated by the computing system run by processor 102 as a smart layer over the camera image 186. The unit size of each box of the scaled grid 190 may have a fixed base reference value which may be for example 1 mm. This value may be scaled in proportion to the camera image keeping the overall aspect ratio fixed.

Figure 5:
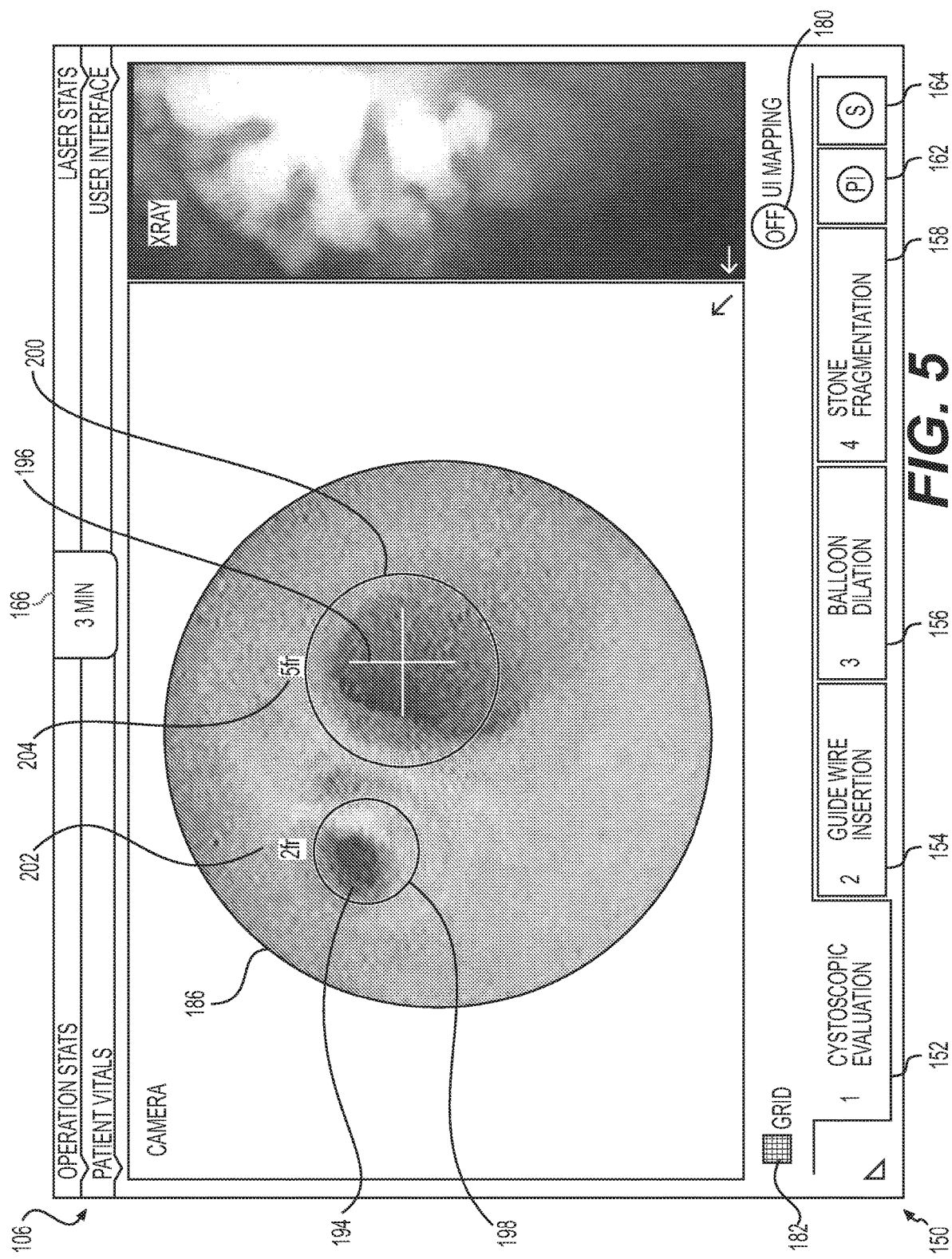

FIG. 5 depicts a user interface displayed on display 106 when an operator activates mapping icon 180. In response to mapping icon 180 being selected by a user, processor 102 may be configured to determine a size of objects disposed within camera field 186. In the image depicted in FIG. 5, two orifices or openings are shown in camera field 186, a first orifice 194 and a second orifice 196. The processor 102 may be configured to recognize the presence of a certain object in the viewing field, such as, e.g., first and second orifices 194 and 196 based on various differentiating features of those orifices. For example, processor 102 may be configured to recognize the color, shape, or other feature of the orifices. Processor 102 may also be configured to compare captured images with a database of images to make determinations based on the comparisons. For example, processor 102 may be able to identify orifices, stones, or other objects in the viewing field based on the similarity of those objects with images stored in a database accessible by process 102. In some examples, however, the user may be required to delineate the outer boundary of the object to be sized, for example, by drawing or otherwise placing virtual boundaries around the objects to be sized. For example, the user may place a first boundary 198 around the image of first lumen 194, and may place a second boundary 200 around the image of second lumen 196. Once the boundaries are placed around the object to be sized, processor 102 may estimate or otherwise determine the size (e.g., diameter) of first orifice 194 and second orifice 196. The determined sizes of those orifices may be overlaidoverlaid onto camera image 186 as values 202 and 204, or may be displayed in another suitable location. For example, the values 202 and 204 may be displayed in a chart or other graphic on display 106 but outside of camera image 186. In one example, process 102 may utilize a reference object of a known size in the field of view to determine the size of another object in the field of view.

Figure 6:
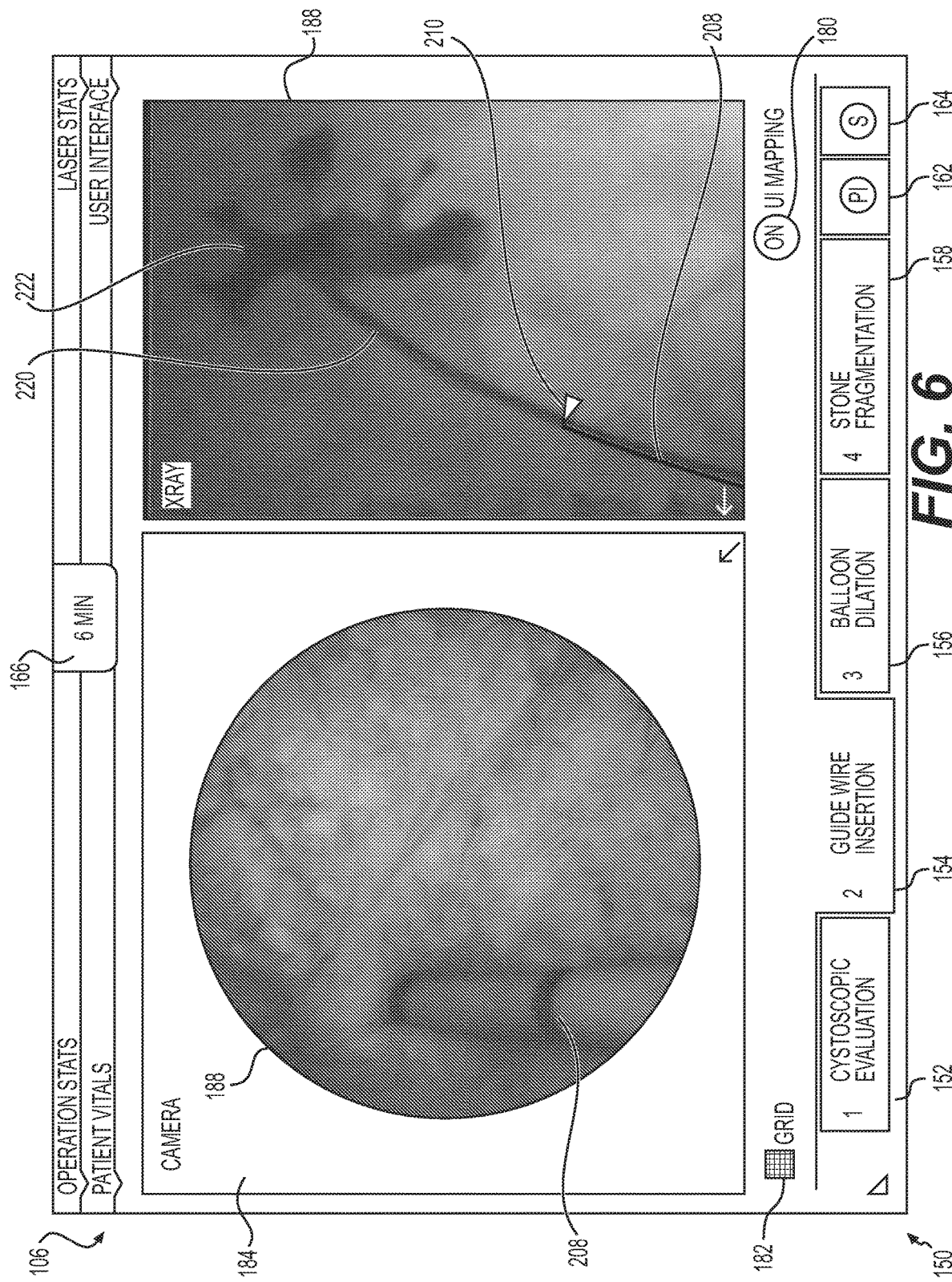

FIG. 6 depicts an exemplary user interface that may be shown on display 106 during a second portion of the lithotripsy procedure, for example, during guide wire insertion. During this stage of the procedure, an operator may position a guidewire through portions of the ureter, bladder, and/or kidney to serve as a track for inserting other tools. The operator may activate tab 154 before inserting the guidewire into the patient, and the activation of tab 154 may cause camera field 184 to display concurrently with x-ray field 188. The operator may then be able to visualize an image of a guidewire 208 collected by, e.g., imaging device 128, while concurrently viewing a representation of guidewire 208 on x-ray field 188. Processor 102 may also be configured to detect the distal end of the guidewire 208 on x-ray field 188, and may place an indicator 210 (e.g., an arrow) at the distal end of the guidewire. Processor 102 may update the position of indicator 210 in real time as the distal end of the guidewire moves through the body.

Figure 7:
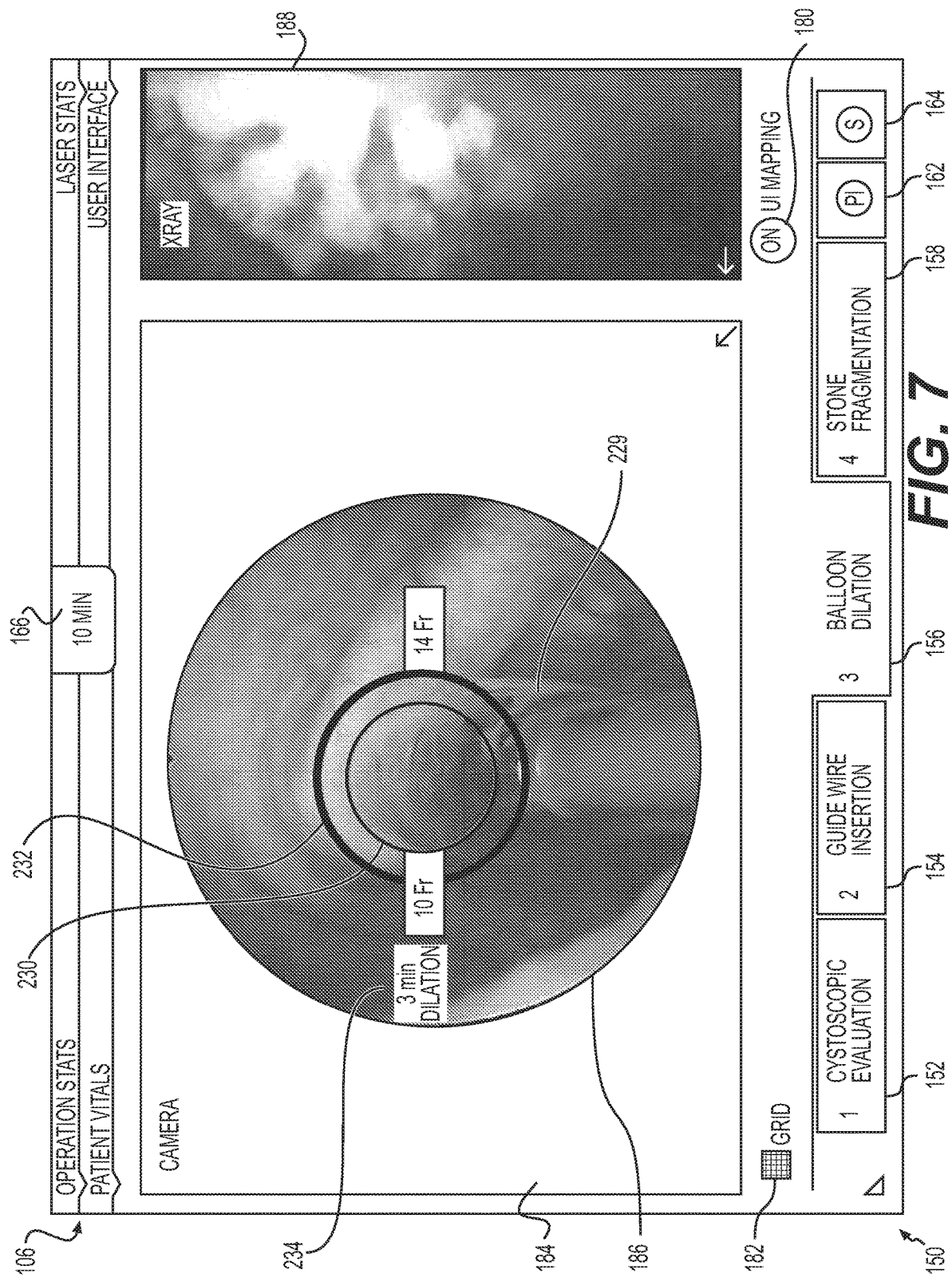

In some lithotripsy procedures, various access points may be too small for the necessary equipment to reach the intended treatment locations, such as, the locations of stones. In such examples, the access points (e.g., orifices and/or lumens) may be enlarged by balloon dilation. FIG. 7 depicts a user interface shown on display 106 during a balloon dilation portion of a lithotripsy procedure. The user interface of FIG. 7 may be shown on display 106 after an operator activates tab 156. In such cases, camera field 184 may be enlarged such that a balloon 229 disposed within the field of view of imaging device 128 is shown on display 106.

During this portion of the procedure, an operator may select mapping icon 180, which may cause processor 102 to analyze the image 186 to recommend a dilation size and length of time that the balloon 229 should be maintained in the dilation mode. For example, a first representation 230 may be overlaidoverlaid on camera image 186, and may represent an estimated or measured size of a body orifice or lumen in the field of view. A second representation 232 may also be overlaidoverlaid on camera image 186 to show the user the size of the lumen that is needed to insert necessary instrumentation through the orifice or lumen. Processor 102 may receive the desired lumen size prior to the start of the lithotripsy procedure or during the lithotripsy procedure from the operator. Processor 102 may also be configured to display a recommendation 234 on the user interface which may correspond to a recommended time for the operator to inflate balloon 229.

The calculation for the suggested time required to dilate the lumen using balloon 229, may require the processor to calculate the difference between the first representation 230 and second representation 232. The inbuilt algorithm may use this data to compare with a standard set of values defined for balloon dilation of the lumen. For example, if the difference is 4 Fr (14 Fr minus 10 Fr) as seen in the camera image 186 (e.g., FIG. 7), the estimated dilation time as suggested by the algorithm may be about 3 minutes. This would be enabled by comparing the value of 4 Fr with the standard value of dilation already built into the system information. In some examples, a maximum delta between actual and desired ID may also trigger a safety alert and advice not to proceed.

While processor 102 may provide recommendations to the operator, the operator may be required to enter a separate instruction to dilate balloon 229 to a certain diameter and for a certain amount of time. In other examples, processor 102 may be configured to proceed to inflate balloon 229 automatically according to this recommendation.

Figure 8:
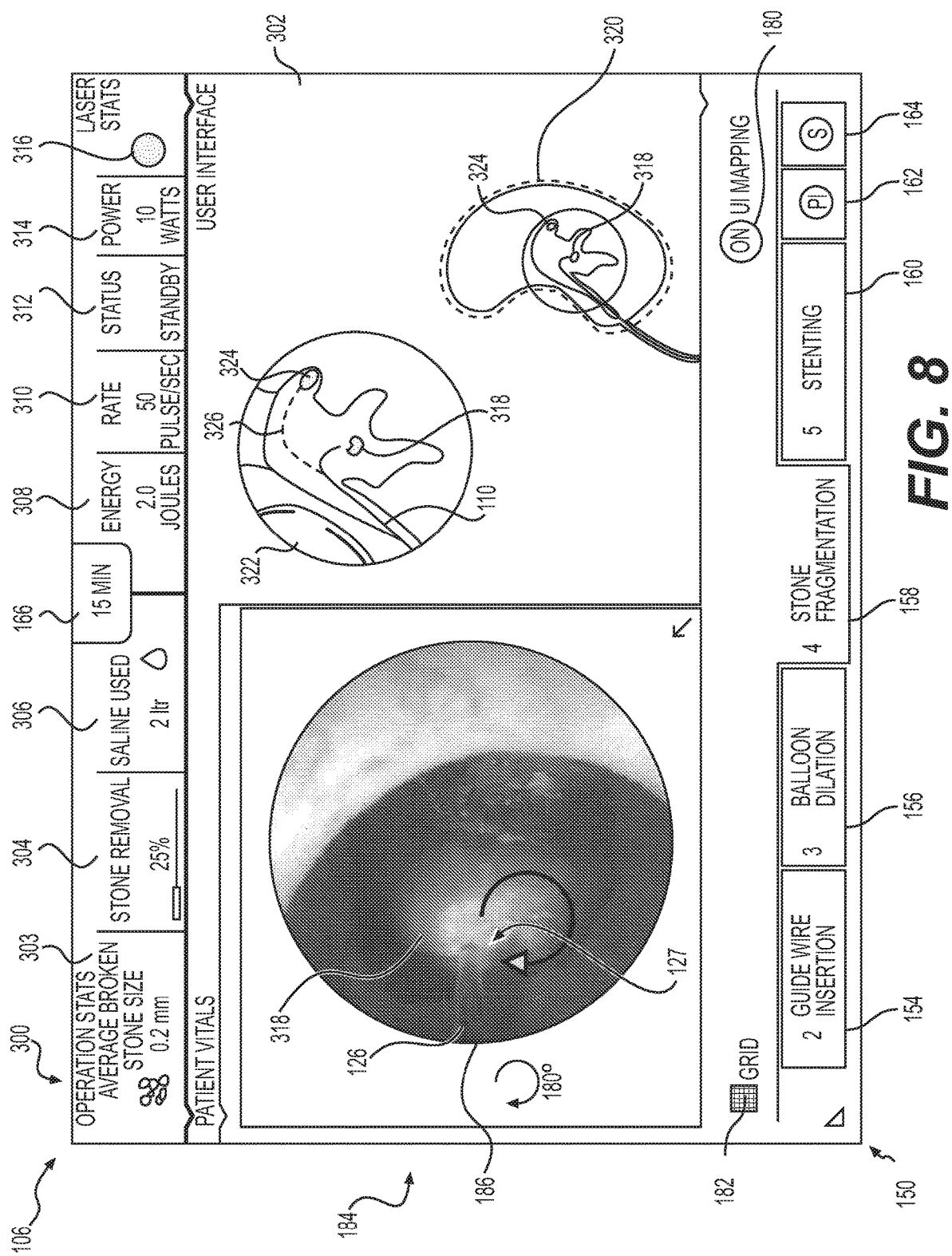
Figure 9:
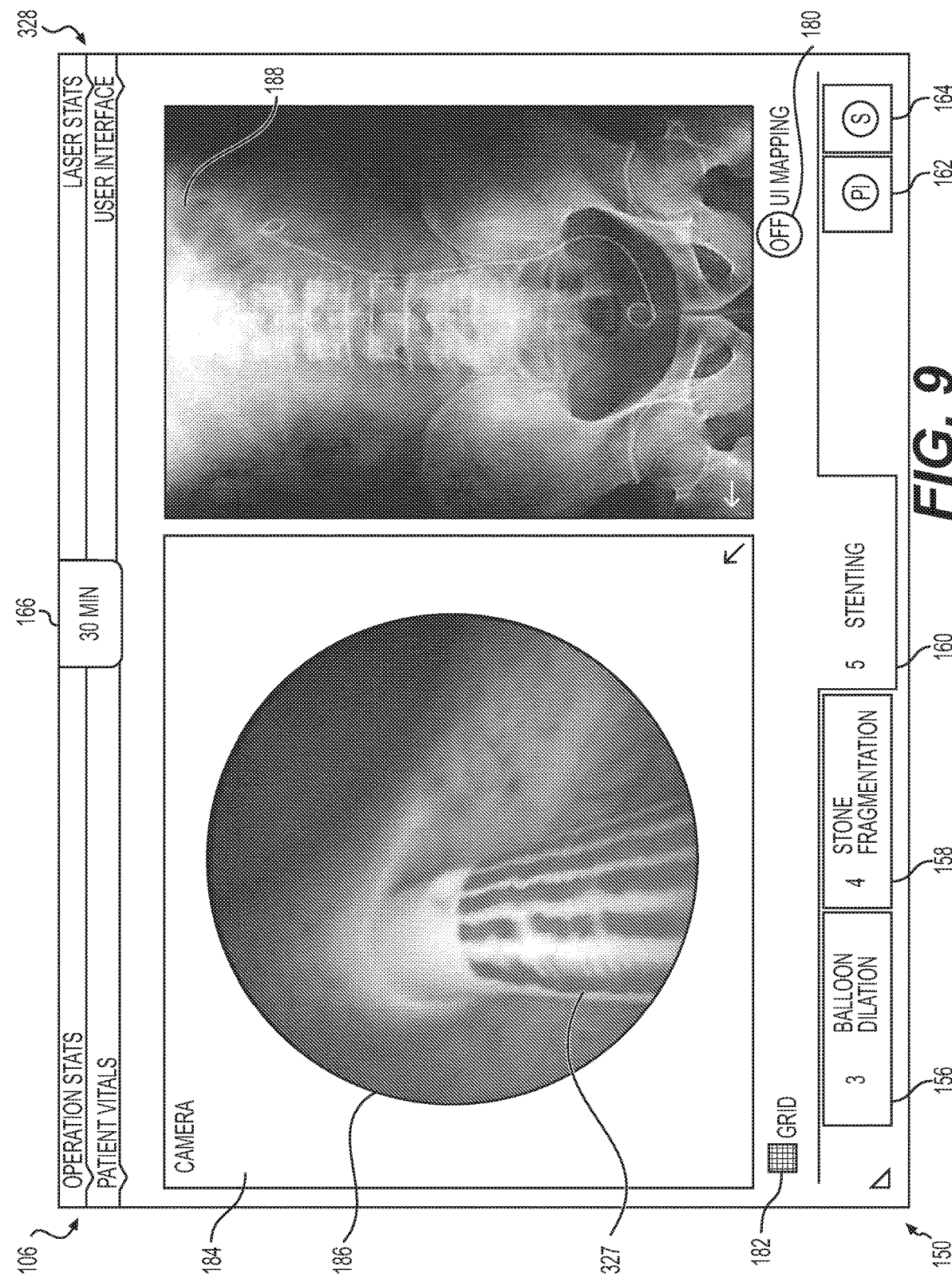

FIG. 8 depicts an exemplary user interface that may be displayed during a stone fragmentation portion of the lithotripsy procedure. This user interface may be displayed once an operator has guided endoscopic device 110 over guidewire 208 to the desired treatment site, and has also activated or selected stone fragmentation tab 158 from procedure section 150 of the user interface. The stone fragmentation user interface may include camera field 184, a fragmentation stats field 300, and a mapping field 302.

At this stage, camera field 184 may depict energy delivery fiber 126, laser energy 127 (during laser delivery), and a stone 318. Fragmentation stats field 300 may depict various parameters and statistics useful to the operator during laser delivery. For example, the average broken stone size 303, a stone removal percentage 304, an amount of saline used 306, the total amount of energy delivered 308, the rate of energy delivery 310, the status of energy delivery 312, the current power level of the laser 314, and an indicator 316 may be shown in fragmentation stats field 300. It is also contemplated that other pertinent information may also be displayed in fragmentation stats field 300. Stone density and type can be input ahead of the procedure based on a diagnostic workup. Stone density may be acquired via analysis of x-ray data preoperatively. Size is also acquired via preoperative CT, preoperative fluoroscopy and/or direct vision. From this information a preloaded table of settings can provide initial settings. As lithotripsy proceeds, the rate and size distribution of fragment generation can be calculated in real time, which may then generate new settings that maximize efficiency of removal. These may be implemented as pop up prompts or as auto-escalating settings.

The processor 102 may be connected to energy device electronics 108 via a CAN BUS connector which may directly fetch the data regarding the energy delivery parameters, and display the same on the display device 106. The CAN BUS connection may also remotely control of the energy delivery parameters on the energy device electronics 108 enabling the urologist direct easy control of the laser energy settings The average broken stone size field 303 may be calculated by processor 102 by analyzing the stone fragments that detach from stone 318. That is, processor 102 may run image analysis software that determines the size of stone fragments that detach from stone 318, and may display the average size of those fragments in field 303. The size of each stone fragment may also be displayed on fragmentation stats field 300, or may be saved by processor 102 for further analysis. The stone removal percentage field 304 may be updated by processor 102 in a similar manner. For example, prior to the initiation of laser delivery to fragment stone 318, processor 102 may run image analysis software of one or more collected images of stone 318 to estimate its size. After laser delivery to stone 318 commences, this value may be continuously updated by continued image analysis as fragments of stone 318 are removed. That is, processor 102 may determine that the stone size is decreasing based on the reduced proportion of the camera field being occupied by the stone.

The fragments of the stone 318 which are flushed out of the system using the used saline fluid may be collected in a strainer. The weight of these fragments may also be measured and communicated to the processor 102. The processor 102 may then compare the weight of the fragments collected with the estimated weight of the stone obtained from initial patient diagnosis or X ray reports as obtained from the HIS and/or EMR. The information regarding the percentage of stone fragments may be displayed on the display device 106 at stone removal percentage field 304.

Processor 102 may update the amount of saline used field 306 based on an input from fluid delivery device 118. Processor 102 may update the total amount of energy delivered 308, the rate of energy delivery 310, the status of energy delivery 312, the current power level of the laser 314, and an indicator 316 based on input from energy delivery electronics 108. Indicator 316 may indicate to the user using one or more colors, whether energy delivery electronics 108 may be activated to deliver energy. For example, a first color, e.g., green, may indicate that energy delivery electronics 108 may be ready to activate while a second color, e.g., red, may indicate that energy delivery electronics is not ready to be activated.

Mapping field 302 may include one or more virtual images of the kidneys, bladder, and/or ureter. In the example shown in FIG. 8, a virtual image 320 of a kidney is shown along with an enlarged virtual image 322 of a portion of the virtual image 320. The virtual images 320 and 322 may show a representation of a first kidney stone 318, along with a virtual image of a second kidney stone 324. The virtual images 320 and 322 may represent a virtual map of the kidneys, bladder, and/or ureter. As the endoscopic device 110 advances through the patient, a locating implement on the endoscopic device 110 may communicate with processor 102 to provide a real position of the device. So long as the virtual map correlates with the actual structure of the organ, an accurate virtual position of the endoscopic device 110 can be displayed on the virtual map on virtual images 320 and 322.

In some examples, treatment parameters of the lithotripsy procedure may be associated with their respective treatment sites to generate a treatment history profile for the patient. This information may be recorded in a memory coupled to processor 102, and may be further transmitted to one or more servers 142 over network 140. This previous treatment history profile may be loaded for use during a subsequent treatment session. Still images or video clips at any point may also be captured locally, removed locally (via, e.g., a thumb-drive), or pushed to cloud or EMR storage.

The parameters may include any of those parameters of values described above, including, but not limited to time or duration of treatment, temperature (of the site, the device, or an adjacent site), energy, power, average power, status/incomplete activations, position of treatment, total energy applied, rate of change in temperature, rate of change in applied energy, amount of saline used, size of stone, average size of broken stone fragments, or a combination thereof. As noted herein, such parameters may be associated with the treatment locations where the parameters were recorded.

As shown in FIG. 8, the virtual images 320 and 322 may track the progress of the endoscopic device 110 as it advances through the kidney. The virtual images 320 and 322 may also visually differentiate treated areas (for example, by shading treated areas) from untreated areas. In addition, the virtual images 320 and 322 may provide visual information to guide the practitioner to the next site (e.g., via a virtual track 326).

After stone fragmentation, an operator may choose to place a stent in the ureter of the patient. In such examples, the operator may select stenting tab 160 to have the user interface shown in FIG. 9 displayed on display 106. This user interface may be substantially similar to previously-described user interfaces, such as the user interface described with reference to FIG. 6. The user interface of FIG. 9 used during a stenting portion of a lithotripsy procedure may simultaneously display a camera field 184 and x-ray field 188. This combination of fields may allow a practitioner to visualize an image of a stent 327 to be placed in the ureter, along with a real-time x-ray image of the stent in x-ray field 188.

Figure 10:
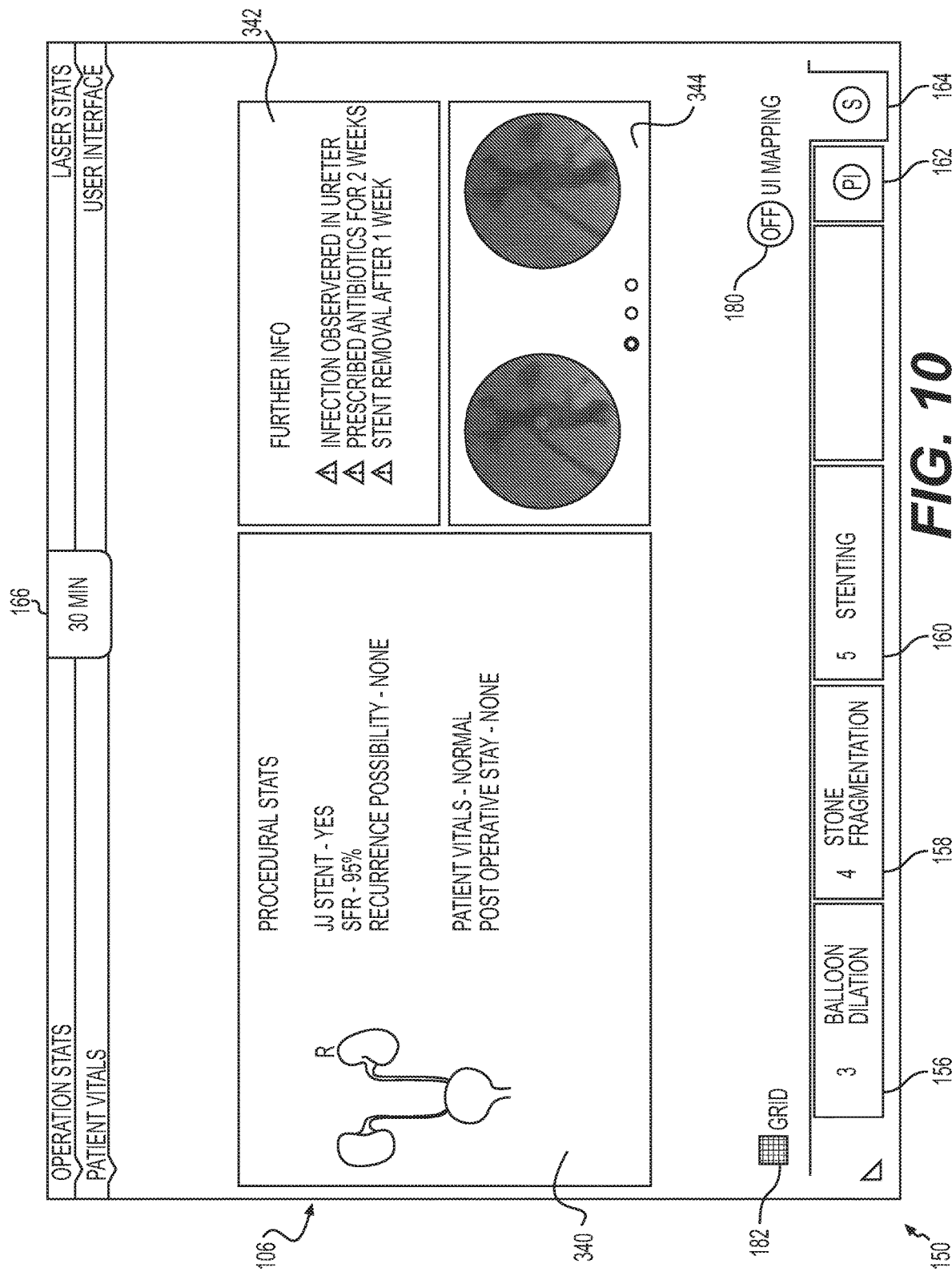

After the conclusion of the lithotripsy procedure, an operator may select summary tab 164, which may cause display 106 to show the user interface depicted in FIG. 10. The summary user interface may include a procedural stats field 340, a further information field 342, and an x-ray field 344. The procedural stats field 340 may display various information such as, e.g., whether a stent was placed, the stone free rate (SFR), the possibility of recurrence of a kidney stone, the patient vitals recorded during the lithotripsy procedure, and whether the patient was kept post-operatively at the treatment facility, among other information. The further information field 340 may display other notes input by the operator over the course of the procedure or after the procedure, such as, e.g., whether an infection was observed within the bladder, kidney, or ureter, whether antibiotics were prescribed, and/or when an implanted stent should be removed. The x-ray field 344 may allow an operator to select one or more x-ray images that were taken during the course of the lithotripsy procedure. In some examples, the operator may view the x-rays taken during the lithotripsy procedure as a video of consecutive images.

Figure 11:
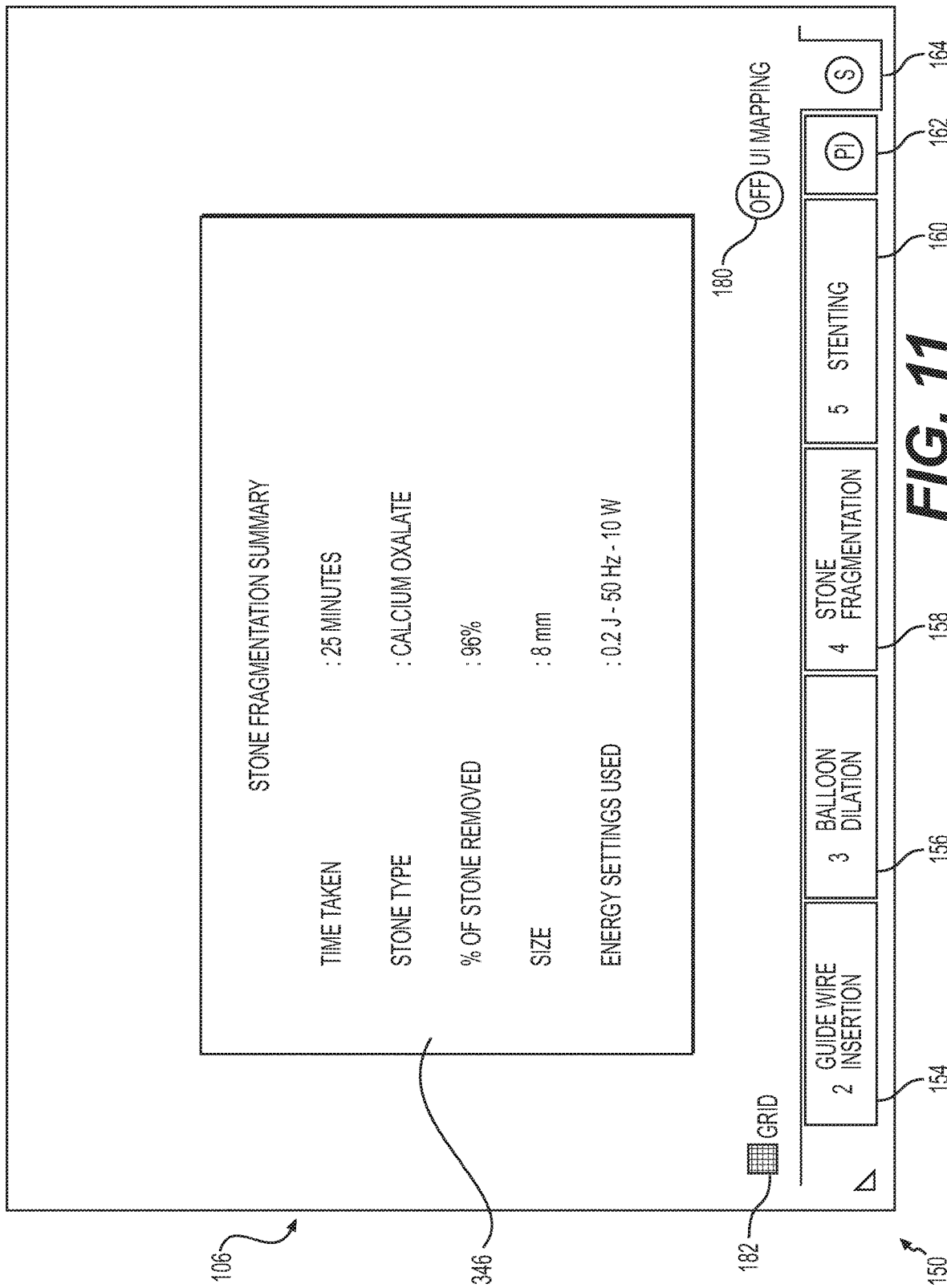

FIG. 11 depicts another user interface that may be accessed after the conclusion of a lithotripsy procedure. The user interface may include a summary field 346 which may display, among other information, the duration of the procedure, the type of stone removed (e.g., a calcium oxalate stone), the percentage of the stone removed, the size of the stone removed, and the various energy settings used during the procedure.

The system and user interfaces disclosed herein may enable physicians and technicians to make faster and smarter decisions to enhance clinical outcomes, reduce procedure time, and reduce cognitive loads required during procedures.

Other examples of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A medical system for use in a medical procedure, comprising:
a processor configured to receive input from a first imaging device, wherein the first imaging device is configured to send image data representative of an image captured within a body lumen to the processor, wherein the processor is configured to:
display the image on a display device coupled to the processor;
analyze the image to sense the presence of an object within the image;
if an object was sensed within the image, analyze the image to estimate a size of the object;
display the estimated size on the display device as a numerical value overlaid onto the image;
display, on the display device, a first user interface before initiation of the medical procedure, wherein the first user interface displays information regarding the patient including at least one of a patient vitals field, a patient stats field, and a diagnosis or anatomy field;
display, on the display device, a second user interface during a first portion of the medical procedure, wherein the second user interface includes the image;
display, on the display device, a third user interface during a second portion of the medical procedure, the second portion of the medical procedure including inserting a guidewire into the lumen, and wherein the third user interface includes both an image and an x-ray image of the guidewire displayed simultaneously on the display device;
display, on the display device, a fourth user interface during a third portion of the medical procedure, the third portion of the medical procedure including estimating a size of an orifice within an image or an x-ray image, and wherein the fourth user interface includes the image or the x-ray image and the estimated size of the orifice overlaid as a numerical value on either the image or the x-ray image;
display, on the display device, a fifth user interface during a fourth portion of the medical procedure, wherein the fourth portion of the medical procedure includes applying laser energy, wherein the fifth user interface includes an image of an energy delivery element delivering laser energy to the object within the lumen;
display, on the display device, a sixth user interface during a fifth portion of the medical procedure, wherein the fifth portion of the medical procedure includes delivering a stent into a lumen of the patient, wherein the sixth user interface includes an image of the stent while disposed within the patient; and display, on the display device, a seventh user interface after the medical procedure has concluded, wherein the seventh user interface includes data relating to the one or more of the first, second, third, fourth, or fifth portions of the medical procedure.

2. The medical system of claim 1, wherein each of the user interfaces on the display device includes a plurality of tabs, and wherein each of the plurality of tabs corresponds to one of the user interfaces and portions of the medical procedure; and wherein the processor is configured to receive a virtual boundary of the object on the displayed image from a user, and wherein the processor is configured to estimate the size of the object based on the virtual boundary.

3. The medical system of claim 1, wherein the processor is configured to compare the image to a database of images to determine the presence of the object within the image.

4. The medical system of claim 1, wherein the object is a ureteral orifice.

5. The medical system of claim 1, wherein the object is a stone, and wherein the processor is configured to update the estimate of the size of the stone in real-time while fragments of the stone are being removed by the application of a laser to the stone.

6. The medical system of claim 5, wherein the processor is configured to update the estimate of the size of the stone based upon a proportion of the image that is occupied by the stone.

7. The medical system of claim 5, wherein the processor is configured to analyze the image to sense when fragments of the stone have been removed by the laser.

8. The medical system of claim 5, wherein the processor is configured to analyze the image to estimate a size of the removed fragments.

9. The medical system of claim 1, wherein the processor is configured to generate a scaled grid that is configured to be overlaid onto the image displayed on the display device.

10. The medical system of claim 9, wherein the scaled grid is representative of an actual size of objects within the image.

11. The medical system of claim 9, wherein the processor is configured to regenerate the scaled grid whenever the processor senses that the first imaging device has been moved.

12. The medical system of claim 9, wherein the processor is configured to receive x-ray data representative of an x-ray image from an x-ray imaging device, and is configured to simultaneously display the image alongside the x-ray image on the display device.

13. The medical system of claim 1, wherein the object is an orifice, and wherein the processor is further configured to analyze the image containing the orifice and generate recommended parameters for inflating a balloon that is inserted into the orifice.

14. The medical system of claim 13, wherein the recommended parameters includes a length of time for inflating the balloon.

15. A method for displaying images relating to a medical procedure, the method including:

analyzing an image received from an imaging device disposed within a lumen of a patient to sense the presence of an orifice within the image;

if the orifice is sensed within the image, further analyzing the image to estimate a size of the orifice;

displaying the estimated size on a display device, wherein the estimated size is displayed as an at least partially numerical value on a scaled grid indicative of the size of the orifice;

sending x-ray data representative of an x-ray image to a processor;

displaying, on the display device, a first user interface before initiation of the medical procedure, wherein the first user interface displays information regarding the patient including at least one of a patient vitals field, a patient stats field, and a diagnosis or anatomy field;

displaying, on the display device, a second user interface during a first portion of the medical procedure, wherein the second user interface includes one or more of the image and the x-ray image;

displaying, on the display device, a third user interface during a second portion of the medical procedure, the second portion of the medical procedure including inserting a guidewire into the lumen, and wherein the third user interface includes both an image and an x-ray image of the guidewire displayed simultaneously on the display device;

displaying, on the display device, a fourth user interface during a third portion of the medical procedure, the third portion of the medical procedure including estimating a size of a second orifice within an image or an x-ray image, and wherein the fourth user interface includes the image or the x-ray image and the estimated size of the second orifice overlaid as a numerical value on either the image or the x-ray image;

displaying, on the display device, a fifth user interface during a fourth portion of the medical procedure, wherein the fourth portion of the medical procedure includes delivering laser energy, wherein the fifth user interface includes an image of an energy delivery element delivering laser energy within the lumen;

displaying, on the display device, a sixth user interface during a fifth portion of the medical procedure, wherein the fifth portion of the medical procedure includes delivering a stent into a lumen of the patient, wherein the sixth user interface includes an image of the stent while disposed within the patient; and displaying, on the display device, a seventh user interface after the medical procedure has concluded, wherein the seventh user interface includes data relating to the one or more of the first, second, third, fourth, or fifth portions of the medical procedure, wherein each of the user interfaces on the display device includes a plurality of tabs, and wherein each of the plurality of tabs corresponds to one of the user interfaces and portions of the medical procedure.

16. The method of claim 15, wherein the method further includes sensing the presence of an object within the image, further analyzing the image to estimate a size of the object, and updating the estimate of the size of the object in real-time while fragments of the object are being removed by the application of a laser to the object.

17. The method of claim 16, further including analyzing the image to sense when fragments of the object have been removed by the laser.

* * * * *